United States Patent [19]

DeBenedictis et al.

[11] Patent Number: 4,935,274
[45] Date of Patent: Jun. 19, 1990

[54] LID STRUCTURE

[75] Inventors: John A. DeBenedictis, West Chester, Pa.; Carl F. Morin, Brandywood; Joshua Benin, Newark, both of Del.; James A. Lawler, Rio Piedras, P.R.

[73] Assignee: E.I. du Pont de Nemours and Company, Wilmington, Del.

[21] Appl. No.: 237,011

[22] Filed: Aug. 26, 1988

[51] Int. Cl.$^5$ .............................................. G01N 1/10
[52] U.S. Cl. .................................. 428/36.7; 206/538; 422/102; 422/310; 428/36.92; 428/349; 428/447; 428/483

[58] Field of Search ................ 422/310, 102; 220/229, 220/359; 428/98, 346, 354, 447, 480, 483, 349, 36.1, 36.8, 36.92; 206/538

[56] References Cited

U.S. PATENT DOCUMENTS 3,850,580 11/1974 Moore et al. ........................ 23/259
4,555,183 11/1985 Thomas ............................. 366/208
4,720,374 1/1988 Ramachandran ................... 422/310

Primary Examiner—James Seidleck

[57] ABSTRACT

A lid structure for a polypropylene container is formed of a three ply laminate and a rehealable silicone rubber top layer adhered to the laminate. The laminate is polyester, polyvinylidene chloride and polypropylene heat sealed to the top rim of the container.

4 Claims, 2 Drawing Sheets

LID STRUCTURE

CROSS REFERENCE TO RELATED APPLICATIONS

Subject matter disclosed herein is disclosed or claimed in the following copending applications filed contemporaneously herewith: Vortexing Liquid Container filed Aug. 26, 1988; Vortex Mixer Drive filed Ser. No. 07/237,017; and Automatic Vortex Mixer, filed Aug. 26, 1988, Ser. No. 07/237,254.

The subject matter disclosed herein is disclosed or claimed in the following copending applications: Resealable Lid Structure for a container, filed July 22, 1985, Ser. No. 757,575 (now U.S. Pat. No. 4,847,050).

FIELD OF THE INVENTION

The present invention relates to a lid structure for a multicompartmented container.

BACKGROUND OF THE INVENTION

It is desirable in automated chemical analyzers to store several reagents in contiguous compartments or vessels. Such a common multicompartment container is sold today for use in an instrument known as the Dimensio ™ Chemical Analyzer by E. I. du Pont de Nemours and Company. Wilmington Del. This multicompartmented container is in the form of a container strip which is described in U.S. Pat. No. 4,720,374 entitled "Container Having a Sonication Compartment". issued to Ramachandran includes a rigid peripheral band formed of an inert plastic. The band is formed integrally with each of the containers such that the container strip generally tapers in a substantially elongated wedge-like manner from a first edge to a second edge. The wedge-shaped plan profile for the container strip facilitates the mounting of a plurality of such strips in a circumferentially adjacent generally radially extending relationship across a rotatable reagent carrying plate. The tops of the containers are sealed with a suitable laminate that prevents gas and vapor escape and yet permits penetration by a probe for aspiration etc. The plastic used for the receptacle is polyethylene and the laminate is a three-ply laminate of a polyester film, a polyvinylidene chloride coating on the polyester film, and finally a sheet of polyethylene adhered to the coating. The laminate is heat sealed to the peripheral surface of the polyethylene compartments with the lower polyethylene sheet contacting the compartment rim.

When storing a liquid reagent or specimen care must be exercised to minimize evaporation. Simultaneously, however whatever structure is used to inhibit evaporation must be compatible with the requirement of access to the liquid as by an aspirating probe during use. The Ramachandran U.S. Pat. No. 4,720,374 entitled "Container Having a Sonication Compartment" describes such a lid which reduces air and vapor transmission through the top of the lid. By isolating the compartments and thereby forming multicompartmented containers, contamination between compartments is also reduced. The lid structure described is formed of conjoined upper and lower sheets of material. The lower sheet is polyethylene and has a receptacle formed therein which receives an elastomeric self-healing pad. The upper sheet is a laminate as described above and the pad is sandwiched between the upper and lower sheets. The portion of the conjoined first and second sheets forms a sealing flange which completely surrounds the periphery of the receptacle and which provides a surface whereby the lid may be secured to the container.

While providing excellent storage for reagents the container strip does not always inhibit evaporative losses after its lid has been punctured by a probe sufficiently to permit its use for the long term on instrument storage of reagents, particularly heterogeneous immunoassay reagents. To facilitate long term or instrument storage the evaporation through the laminate should be less than one milligram per day. Such a low rate would permit even such immunoassay reagents to be stored for more than ten days on the instrument. Such low evaporation must subsist despite repeated puncturing of the laminate for the aspiration of fluids.

It is known that creating a vortex in the fluid contained in a compartment is an effective means for mixing the contents of the vessel. Common laboratory vortexers use a support cup or a resilient compartment receiving surface mounted eccentrically to a motor in order to translate the compartment in a circular path or orbit at a high speed and thereby create an effective vortex in the fluid contained in the compartment. Exemplary of this type of device are those disclosed in U.S. Pat. Nos. 4,555,183 (Thomas) and 3,850,580 (Moore et al.). These devices are manual in that an operator is required to hold the compartment in contact with the eccentrically movable means to create the vortex in the fluid disposed in the compartment.

Such vortex type mixer would be extremely advantageous in an automated chemical analysis instrument as it is noninvasive and therefore can avoid the concern of contamination associated with an improperly cleaned invasive mixing means.

Unfortunately, when the bottom of a vessel or compartment is orbited to create a vortex, it is difficult to maintain the compartment's lid structure sealed. This is particularly true when these are multicompartments and one is orbited and the others remain stationary.

SUMMARY OF THE INVENTION

Many of these problems of long term storage. high evaporation rate, and evaporative loss due to puncturing of the laminate are solved by the lid structure of this invention. According to a preferred embodiment of this invention there is provided a lid structure (for a compartment formed of a first chemically inert plastic and having a peripheral mounting surface thereon) comprising a three ply laminate of a polyester film a polyvinylidene chloride coating on the polyester film and a sheet of the first plastic adhered to the coating the laminate being sealed to the peripheral surface with the first plastic sheet connected to such surface, and a self-healing sheet of elastomer material adhered to the polyester film.

Preferably the first plastic is polypropylene, although polyethylene may be used. The elastomer layer preferably is silicone rubber. This combination affords a lid for a compartment or multi-compartmented container that seals the compartment(s), and is penetrable easily by a probe, non-coring, and self-healing. A compartment with such a lid has a low evaporation rate. The lid is chemically inert, and can provide little or no adhesive transfer.

BRIEF DESCRIPTION OF THE DRAWINGS

The invention may be more fully understood from the following detailed description thereof taken in connection with the accompanying drawings which form a part of this application and in which similar reference numbers refer to similar elements in all figures of the drawings in which.

DETAILED DESCRIPTION OF THE INVENTION

Figure 1:
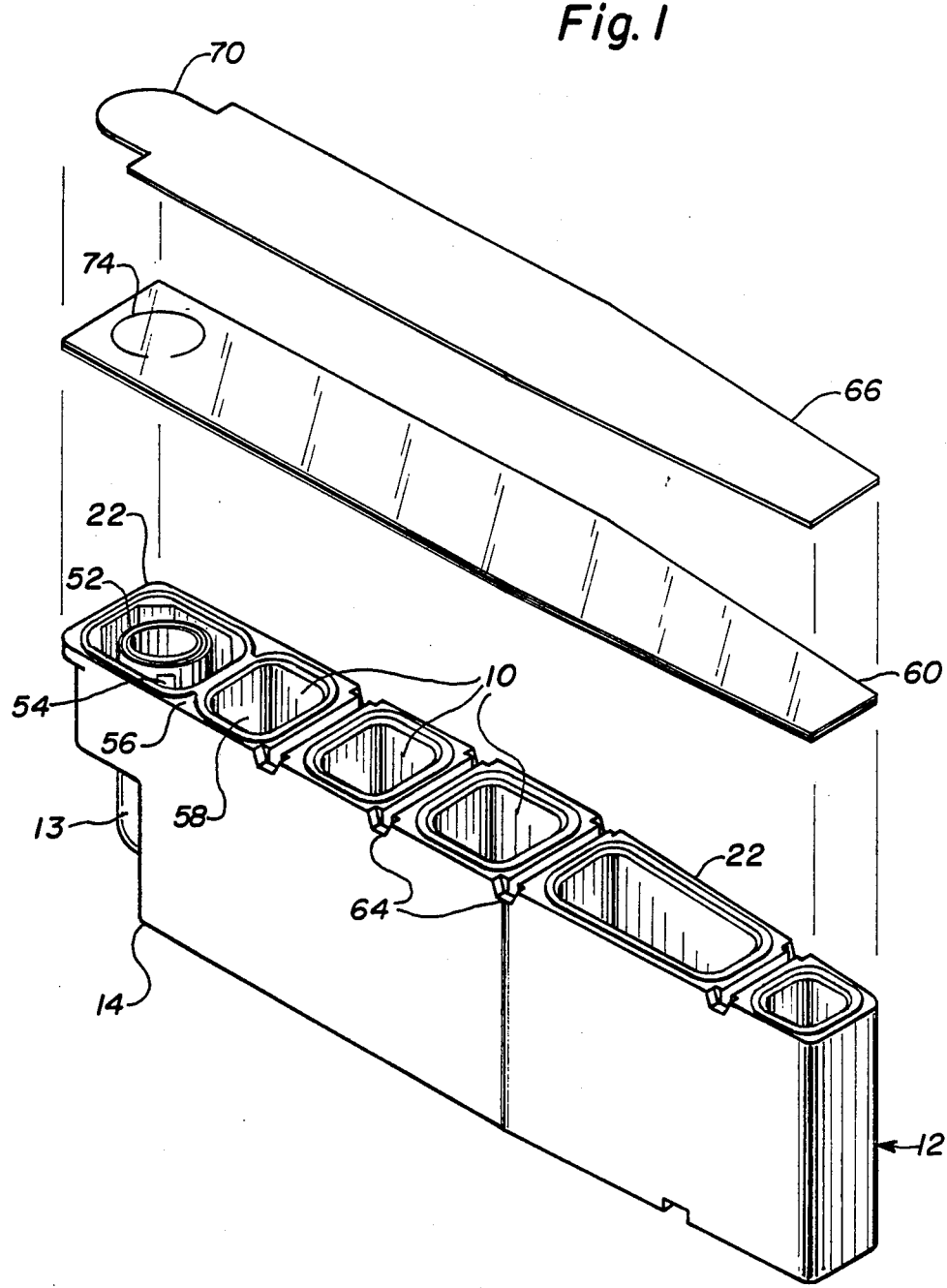
FIG. 1 is an exploded view of a multicontainer strip that is useful for holding liquids for chemical testing in which each container defines a compartment capable of holding reagents in either liquid or lyophilized (tabletted) form.
Figure 2:
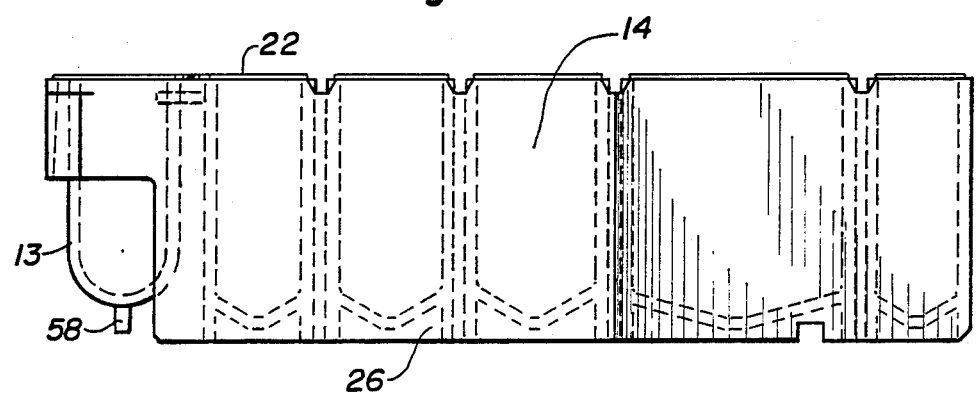
FIG. 2 is a side elevation view of the multicontainer strip of FIG. 1.
Figure 3:
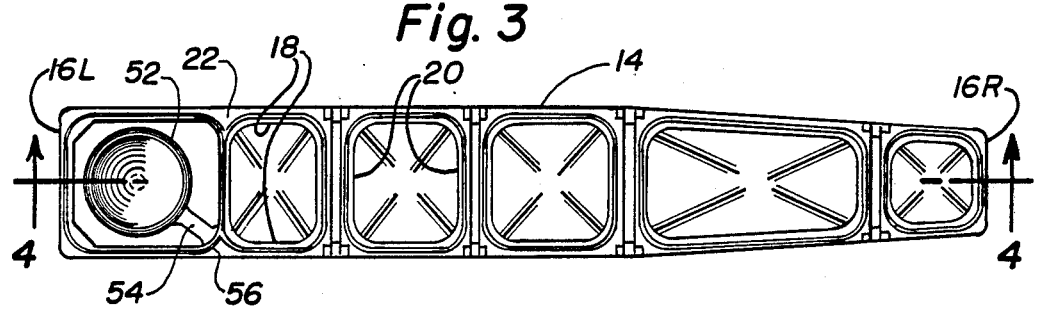
FIG. 3 is a plan view of the multicontainer strip depicted in FIG. 1.
Figure 4:
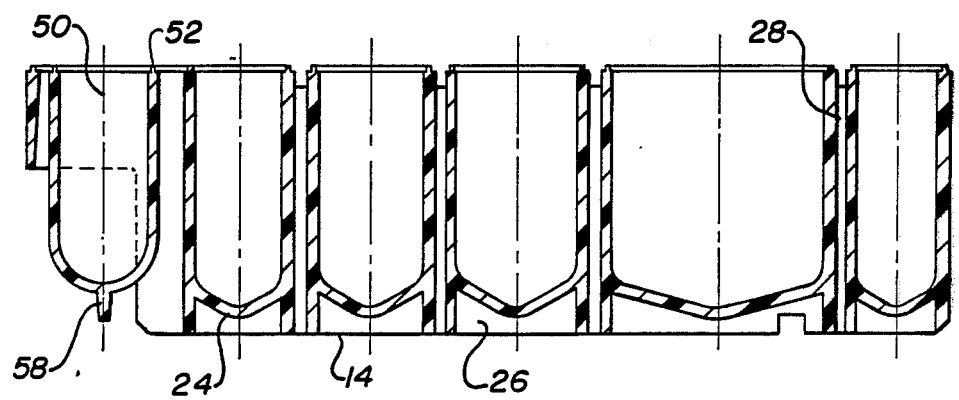
FIG. 4 is a cross-sectional side elevation view of the multicompartmented strip taken through the sectional line 4—4 of FIG. 3.

As may be seen in FIG. 1 a plurality of containers 10 are arranged in an end-to-end relationship to form a container strip generally indicated by the reference character 12. The container strip 12 may be fabricated in any convenient manner. In the embodiment shown, the container strip 12 includes a rigid peripheral band 14 formed of a suitable material such as an inert plastic. The band 14 is either joined to or preferably is formed integrally with each of the containers 10 such that in the preferred case the container strip 12 generally tapers in a substantially elongated wedge-like manner from a first edge 16L to a second edge 16R (FIG. 3). This wedge-shaped plan profile for the container strip 12 facilitates the mounting of a plurality of such strips in a circumferentially adjacent, generally radially extending relationship across a rotatable reagent carrying plate such as that the analysis instrument disclosed in pending application Ser. No. 07/139108, filed Dec. 12, 1987, entitled "Analysis Instrument Having Heat-Formed Analysis Cuvettes" (IP-0473). Such usage is also described in copending application entitled "Method and Apparatus for Effecting the Automatic Analytical Testing of Samples, Ser. No. 07/237,119 filed Aug. 26, 1988. It should be appreciated however that the individual containers may take any predetermined configuration and may be used alone or arranged together in any convenient number and remain within the contemplation of this invention.

As is described in the '374 patent each of the containers can be arranged singularly or in a container strip 12 and is formed of a suitable inert plastic material. Each container 10 includes a compartment defined by generally opposed pairs of generally parallel and integrally formed sidewalls 18 and endwalls 20. The upper surfaces of the sidewalls 18 and the endwalls 20 together with the upper surface of the band 14 in the vicinity thereof register to define a substantially planar sealing surface 22 peripherally surrounding the open upper end of the containers 10. Each of the containers 10 except for an end vortexing container 13 is closed by a downwardly sloping inverted pyramidal floor 24.

In the preferred embodiment, the sidewalls 18 of each container 10 except for the vortexing container 13 are joined to and integral with the peripheral band 14. The band 14 extends slightly below the lower ends of the containers 10 and thus defines a support structure 26 whereby the strip may be set on a suitable work surface. The several containers 10 may be arranged in various configurations square rectangular, etc.

Each of the adjacent containers 10 are spaced from each other by a predetermined gap 28 to enhance the thermal and vapor isolation of each of the containers and permits the integrity of the seal for each container. Preferably the container strip 12 is formed by injection molding and is formed of polypropylene. Alternatively polyethylene or other suitable materials of construction may be used, however polypropylene is preferred because of its ability to be flexed many times and not break. This facilitates the operation of the vortexing container 13.

The end compartment which defines the vortexing container 13 is tubular and elongated and has a longitudinal axis 50. The end compartment 13 also has a rim 52 which defines a peripheral mounting surface similar to the peripheral mounting surfaces provided by the containers 10 and the band 14. The compartment 13 is connected to the band 14 by an integral thin finger of plastic forming a flexible hinge 54. The flexible hinge 54 is directed to a corner 56 formed by the band 14 and the end container. The plastic finger is located just below the rim 52 such that it does not interfere with the vapor seal laminate which is placed on top of the vortexing container 13 and the containers 10 and to prevent its being affected by the heat sealing process. The bottom of the container 13 is formed to have a downwardly extending protuberant tip portion 58 which is adapted to being engaged by an eccentric or orbiting type drive to create nutational movement of the bottom portion of the vortexing container 13 the container 13 pivoting about the flexible hinge 54. The lower portion of the band 14 is cut back in the region of the container 13 to form a short skirt about the container 13 such that the container 13 is free for such nutational movement at its lower portion.

A suitable drive for the protuberant tip 58 to provide such nutational motion is described in copending application Ser. No. 07/237,254, filed Aug. 26, 1988 and entitled "Drive for Reagent Container". An alternative drive that may be used is that described in an article Wada et al., Automatic DNA Sequencer: Computer-programmed microchemical manipulator for the Maxam-Gilbert sequencing method, Rev Sci. Instrum., 54(11). 1969-1572. Since the particular drive does not form a part of this invention it will not be described further except to say that the function of the drive is to engage the protuberant tip and move it in an nutational or orbital type movement so as to establish vortex mixing within the container 13.

While the container 13 may be left open if desired, for the reasons previously stated, when reagents are stored therein it is best that a vapor barrier and a rehealable lid be used to accommodate plural piercings by a probe for withdrawal of the reagents, etc.

According to this invention a three-ply laminate 60 is heat-sealed to the peripheral mounting surfaces of the containers 10 including the vortexing container 13, and the band 14 particularly where it forms a skirt about the rim 52 of the compartment 13. To facilitate sealing of the individual containers i.e., compartments, a small notch 64 is formed in the band 14 in the molding process between each container but for the container adjacent the vortexing container 13. Finally, a self-healing lid structure 66 is adhered to the laminate 60.

The self-healing structure 66 may be any of the elastomers that are chemically inert. It is preferred however that a silicon rubber sheet, having a thickness of about 32 mils, sold by CHR Industries be used. It is applied to the laminate 60 with a suitable adhesive such as that available from the General Electric Company of Waterford N.Y. having a product identification of TSA6574 which is a silicone resin which uses a primer solution having a product identification of SR500. Alternatively, an acrylic resin adhesive may be used. The end of the lid structure 66 which is over the container 13 has its exterior cutaway to form a semicircular end 70 having the same diameter and width as that of the vortexing container 13. Further, in accordance with the preferred embodiment of this invention the laminate 60 is slit 74 immediately about the rim 52 prior to application of the lid structure 66 to facilitate the nutational movement of the container 13 without disturbing the seal.

The laminate closes each of the containers with an impermeable seal so as to form an evaporation barrier for the contents of the container 13 and the containers 10 and to isolate the containers against vapor cross contamination and isolate the containers from outside contaminating gasses such as carbon dioxide or oxygen.

Since the laminate 60 is heat sealed to the mounting surfaces provided by each container, the material of the lower laminate ply must be heat sealable to the plastic forming the strip 14. In its preferred embodiment the laminate 60 is three-ply laminate with the outer layer a polyester film such as that sold by E. I. du pont de Nemours and Company under the trademark Mylar ®, a polyvinylidene chloride coating on the polyester film such as that sold by Dow Chemical Co. under the trademark Saran ®, and finally an outer barrier sheet of polypropylene since the strip is made of polypropylene. If the strip were made of polyethylene this lower laminate ply would be polyethylene.

The lid structure 66 may be provided with slits to facilitate the insertion of probes into the compartment 12 and containers 10. The use of the silicon rubber seal which is a self-healing elastomer provides a wiping action on the probe, does not tend to stick to the probe, is not easily cored and is easily penetrable.

The invention described has the advantages of providing a suitable vapor and gas barrier such that reagents even after hydration may be stored in the several containers 10, 13 for many days without significant evaporation or vapor contamination. This is particularly relevant when the reagents are those used with immunoassays which can be relatively critical and where an evaporation rate of less than 1 milligram of solution per day is permitted without affecting the integrity of the reagents. Furthermore the seal is not disturbed by the nutational movement of the compartment 12. Such nutational movement is particularly facilitated by the slitting of the laminate about the top rim 52 of the compartment and by die cutting the lid structure around the rim of the movable well as described.

We claim:

1. A reagent storage device comprising:
   a multi-compartmented strip of containers integrally formed of a first chemically inert plastic and having a peripheral mounting surface, at the top of each container, and
   a lid structure for the strip of containers formed of:
   a three ply laminate of a polyester film, a polyvinylidene chloride coating on the polyester film, and a sheet of a first plastic adhered to the coating, the laminate being sealed to the peripheral surface of each container with the first plastic sheet connected to such surface, and
   a single self-healing sheet of elastomer material adhered to the polyester film.

2. A storage device as set forth in claim 1 wherein the first plastic is polypropylene.

3. A storage device as set forth in claim 1 wherein the first plastic is polyethylene.

4. A storage device as set forth in claim 1 wherein the elastomer material is silicone rubber which is adhered to the polyester film by a silicone adhesive.

* * * * *